United States Patent
Tissandier

(10) Patent No.: US 9,726,653 B2
(45) Date of Patent: Aug. 8, 2017

(54) CHEMICAL DETECTOR

(71) Applicant: Hamilton Sundstrand Corporation, Charlotte, NC (US)

(72) Inventor: Michael D. Tissandier, Alta Loma, CA (US)

(73) Assignee: HAMILTON SUNDSTRAND CORPORATION, Charlotte, NC (US)

( * ) Notice: Subject to any disclaimer, the term of this patent is extended or adjusted under 35 U.S.C. 154(b) by 453 days.

(21) Appl. No.: 14/225,964

(22) Filed: Mar. 26, 2014

(65) Prior Publication Data

US 2015/0276560 A1      Oct. 1, 2015

(51) Int. Cl.
| | |
|---|---|
| *G01N 1/22* | (2006.01) |
| *G01N 33/00* | (2006.01) |
| *G01N 1/28* | (2006.01) |
| *G01N 1/44* | (2006.01) |

(52) U.S. Cl.
CPC ....... *G01N 33/0036* (2013.01); *G01N 1/2208* (2013.01); *G01N 1/28* (2013.01); *G01N 1/2202* (2013.01); *G01N 1/2813* (2013.01); *G01N 1/44* (2013.01); *G01N 2001/2223* (2013.01)

(58) Field of Classification Search
CPC .. G01N 1/22; G01N 33/00; G01N 2001/2223; G01N 1/2202; G01N 1/405; G01N 2291/0256; G01N 5/02; H01J 49/0422; B05B 9/002
USPC ............... 73/28.04, 863.12, 23.2, 53.01, 159
See application file for complete search history.

(56) References Cited

U.S. PATENT DOCUMENTS

| | | | |
|---|---|---|---|
| 4,542,641 A | 9/1985 | Eyler | |
| 4,819,719 A | 4/1989 | Grote | |
| 5,904,900 A * | 5/1999 | Bleuse | G01N 1/02 422/530 |
| 6,511,760 B1 * | 1/2003 | Barone | C23C 16/0254 148/279 |
| 6,641,648 B2 | 11/2003 | Walker et al. | |
| 6,978,657 B1 * | 12/2005 | Baumann | G01N 1/2214 73/28.04 |
| 7,113,277 B2 | 9/2006 | Craig | |
| 7,282,676 B1 * | 10/2007 | Bouchier | H05B 1/0247 219/492 |

(Continued)

FOREIGN PATENT DOCUMENTS

| | | | | |
|---|---|---|---|---|
| GB | WO 2008110845 A3 * | 7/2009 | | H01J 49/0409 |
| GB | 2518509 A | 3/2015 | | |

(Continued)

OTHER PUBLICATIONS

Great Britain Search Report for application No. GB1505190.7; Mailing Date Dec. 24, 2015, 6 pages.

*Primary Examiner* — Hezron E Williams
*Assistant Examiner* — Gedeon M Kidanu
(74) *Attorney, Agent, or Firm* — Cantor Colburn LLP

(57) ABSTRACT

A chemical detector is provided and includes a chemical detector device and a chemical agent aerosol vaporizer assembly. The chemical agent aerosol vaporizer assembly includes a vaporizer fluidly interposed between an inlet and an outlet and is configured to receive via the inlet a chemical agent aerosol in the vaporizer wherein the chemical agent aerosol is smeared against a fluted surface that is passivated against adsorption and vaporized. The vaporized chemical agent aerosol is subsequently output to the chemical detector device via the outlet.

16 Claims, 3 Drawing Sheets

(56) References Cited

U.S. PATENT DOCUMENTS

| | | | |
|---|---|---|---|
| 7,299,709 B1 | 11/2007 | Grove | |
| 7,299,711 B1 * | 11/2007 | Linker | G01N 1/2214 |
| | | | 73/863.23 |
| 7,304,742 B1 | 12/2007 | Gurton | |
| 7,339,165 B2 | 3/2008 | Donaldson et al. | |
| 7,400,940 B2 | 7/2008 | McRae et al. | |
| 7,540,286 B2 * | 6/2009 | Cross | A61M 15/0045 |
| | | | 128/203.26 |
| 7,837,937 B2 | 11/2010 | Donaldson et al. | |
| 7,977,113 B2 | 7/2011 | Donaldson et al. | |
| 8,225,681 B2 | 7/2012 | Paur et al. | |
| 8,520,205 B2 * | 8/2013 | Silcott | G01N 15/0618 |
| | | | 356/318 |
| 2004/0159319 A1 * | 8/2004 | Kadel | B01D 39/16 |
| | | | 128/200.18 |
| 2007/0180017 A1 | 8/2007 | Weber | |
| 2008/0014589 A1 | 1/2008 | Link et al. | |
| 2011/0155153 A1 * | 6/2011 | Thorens | H05B 3/58 |
| | | | 131/329 |
| 2012/0120392 A1 * | 5/2012 | Ewing | G01N 1/405 |
| | | | 356/301 |

FOREIGN PATENT DOCUMENTS

| | | | |
|---|---|---|---|
| WO | 9843063 A1 | 10/1998 | |
| WO | WO 9843063 A1 * | 10/1998 | G01N 1/2214 |

* cited by examiner

CHEMICAL DETECTOR

BACKGROUND OF THE INVENTION

The subject matter disclosed herein relates to a chemical detector and, more particularly, to a chemical detector including a chemical agent aerosol vaporizer.

Chemical agents often exist as liquids at room temperature. Dispersal of these agents often results in aerosols of oily droplets rather than vaporous clouds. Chemical detectors are typically dependent, however, on the presence of vapor for detection and thus may not function properly or effectively in the absence of vapor. In addition, the inlet systems for chemical detectors tend to operate in the laminar flow regime to prevent loss of vapors to the inlet walls due to an increase in carrier surface interactions through turbulence. Unfortunately, aerosols in a laminar flow regime that have only minimal interactions with wall surfaces may not experience any added effects from surface area increases of the droplets.

To address these issues, some chemical detectors use a fine wire screen in the sample path to capture aerosol droplets. The screen is heated to vaporize the captured droplets whereupon the resultant vapor can be directed toward a downstream detector device. Drawbacks to these systems include the fact that the screen needs to be of sufficiently fine mesh to ensure that a large fraction of particles impact on the heated wires, but the fine mesh is relatively easily fouled by atmospheric particulates, such as dust, when operations are undertaken outside of a laboratory environment.

BRIEF DESCRIPTION OF THE INVENTION

According to one aspect of the invention, a chemical detector is provided and includes a chemical detector device and a chemical agent aerosol vaporizer assembly. The chemical agent aerosol vaporizer assembly includes a vaporizer interposed between an inlet and an outlet and is configured to receive via the inlet a chemical agent aerosol in the vaporizer wherein the chemical agent aerosol is smeared against and vaporized by a fluted surface that is passivated against adsorption. The vaporized chemical agent aerosol is subsequently output to the chemical detector device via the outlet.

According to yet another aspect of the invention, a chemical agent aerosol vaporizer assembly is provided and includes an inlet, an outlet, a vaporizer interposed between the inlet and the outlet and a heated, fluted surface disposed within the vaporizer such that a chemical agent aerosol, which is received in the vaporizer via the inlet, is smeared against and vaporized by the heated, fluted surface, which is passivated against adsorption. The vaporized chemical agent aerosol is subsequently output from the vaporizer via the outlet.

These and other advantages and features will become more apparent from the following description taken in conjunction with the drawings.

BRIEF DESCRIPTION OF THE DRAWINGS

The subject matter, which is regarded as the invention, is particularly pointed out and distinctly claimed in the claims at the conclusion of the specification. The foregoing and other features, and advantages of the invention are apparent from the following detailed description taken in conjunction with the accompanying drawings in which:

The detailed description explains embodiments of the invention, together with advantages and features, by way of example with reference to the drawings.

DETAILED DESCRIPTION OF THE INVENTION

Some chemical agents are amenable to dispersion as condensed phase aerosols rather than as vapor, either due to an inherent low volatility or by being intentionally formed to evade detection. Indeed, chemical agent detection systems typically rely on gas phase samples (non-condensed) for detection and quantitation of the agent. If the agent is presented as an aerosol, the small amount of material in the vapor phase above the aerosol particle may not be representative of the amount of agent present (quantitation) and may not present sufficient material to the detector for an alarm to be triggered (detection). Conversion of the aerosol particle into non-condensed material for detection allows existing detection schema to detect the presence of agent without modification of the detection methodology directly.

To this end, as will be described below, an agent aerosol laden sample stream is directed toward an enclosed cavity containing a fluted surface. The surface is passivated against adsorption and heated. As the aerosol droplets reach the flutes, they impact at a high impact parameter and the liquid droplets, such as the majority of chemical agent aerosols, tend to deform and "smear" against the surface creating a much larger surface area than the original droplet and a resultant higher volume of vapor due to increased surface area and the higher temperature of the surface. Solid droplets will either (depending on velocity and particle size) impact on the surface and stick or "bounce" into the flute groove. In both cases, a temperature of the particle will be increased to generate more vapor for downstream analysis.

Figure 1:
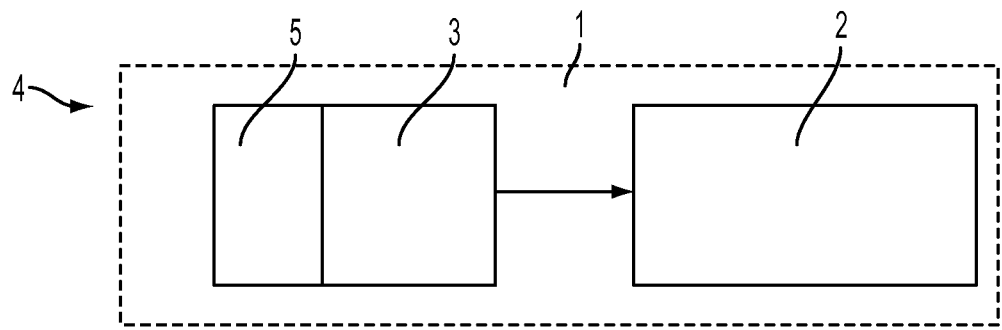
FIG. 1 is a schematic diagram of a chemical detector in accordance with embodiments.
Figure 2:
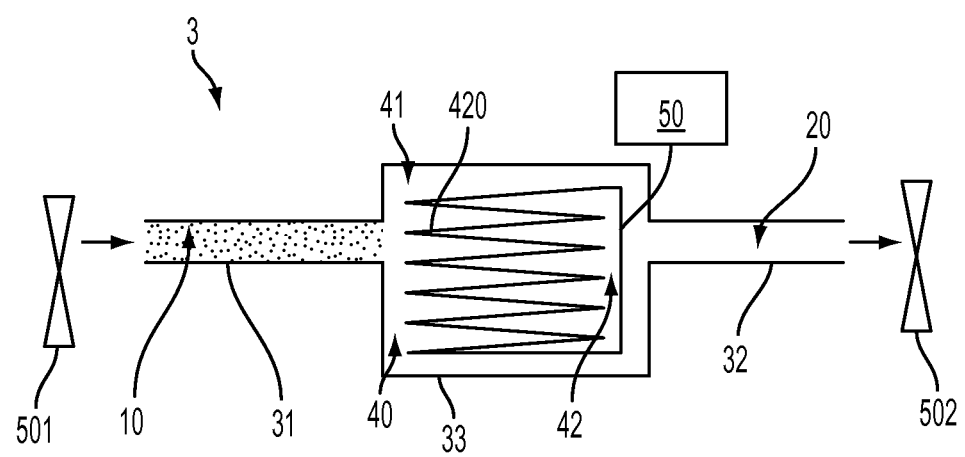
FIG. 2 is side view of a chemical agent aerosol vaporizer assembly of the chemical detector of FIG. 1 in accordance with embodiments.
Figure 3:
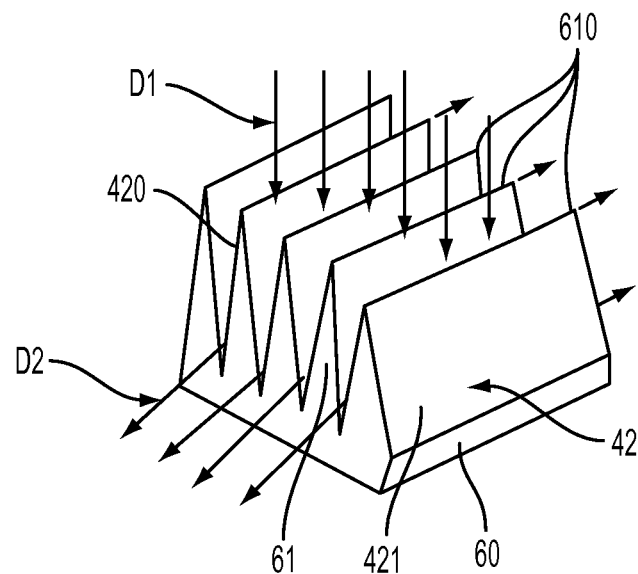
FIG. 3 is a perspective view of a vaporizer element in accordance with embodiments.

With reference to FIGS. 1-3, a chemical detector 1 is provided and includes a chemical detector device 2 and a chemical agent aerosol vaporizer assembly 3. The chemical detector device 2 is configured to detect a chemical agent. The chemical detector device 2 generally operates most efficiently when the chemical agent is in vaporized form and is present in a relatively high concentration that is representative of the concentration of the chemical agent in an exterior space 4 surrounding the chemical detector 1.

The chemical agent aerosol vaporizer assembly 3 includes a first wall portion 31 formed to define an inlet 10, a second wall portion 32 formed to define an outlet 20 and a central wall portion 33 formed to define a vaporizer 40. The vaporizer 40 is fluidly interposed between the inlet 10 and the outlet 20 and defines an interior 41 in which a vaporizer element 42 is disposable. The chemical agent aerosol vaporizer assembly 3 is thus configured to receive a chemical agent aerosol via the inlet 10 such that the chemical agent aerosol enters into the vaporizer 40. Within the vaporizer 40, the droplets of the chemical agent aerosol flow in a first direction D1 and eventually come into contact with and are smeared against a fluted surface 420 of the vaporizer element 42.

The fluted surface 420 is passivated against adsorption and absorption of the material of the droplets of the chemical agent aerosol into the vaporizer element 42. The passivation process can be designed to passivate the fluted surface 420 against all or some chemicals agent aerosols and may be similar to the processes described in U.S. Pat. Nos. 6,511,760 and 6,444,326, the disclosures of which are incorporated herein in their entireties. In the latter passivation case where the fluted surface 420 is passivated against some chemical agent aerosols, differently passivated fluted surfaces 420 may be provided such that they are replaceable/interchangeable with one another based on a particular chemical agent aerosol being tested for at a given instance.

In accordance with embodiments, the fluted surface 420 may be formed of glass, glass-like material or another similar material. In accordance with further embodiments, the fluted surface 420 may be formed of quartz, coated stainless steel (the coating may include, e.g., Silcosteel™, Siltek™ or Sulfinert™) or highly polished stainless steel. In accordance with still further embodiments, a material of the fluted surface 420 may be inert or, more particularly, inert with respect to the chemical agent being detected. In accordance with still further embodiments, as noted above, the material of the fluted surface 420 may be replaceable for detection of various chemical agents. It is to be understood that a person of skill in the art would know that a certain fluted surface 420 material would be passive against certain chemical agent aerosols.

The fluted surface 420 is also heated by a heating element 50 coupled thereto. In accordance with embodiments, the heating of the fluted surface 420 may increase a temperature of the fluted surface 420 to 150 degrees Fahrenheit or higher although it is to be understood that the degree of heating can be varied for the type of chemical agent being detected. That is, the degree of heating can be increased for a chemical agent that has a high minimum vaporization temperature or further increased for a chemical agent that has an even higher minimum vaporization temperature.

With the droplets of the chemical agent smeared against the fluted surface 420 of the vaporizer element 42 but not adsorbed into the vaporizer element 42, and with the fluted surface 420 being heated by the heating element 50, the surface area of the droplets contacting the fluted surface 420 is increased such that the heating of the fluted surface 420 vaporizes all or a substantial fraction of each of the droplets. The vaporized chemical agent aerosol is subsequently driven in a second direction D2 by the pressure of the trailing vaporized chemical agent aerosol and by a driving element 5 (to be described below), which is transversely oriented relative to the first direction D1, toward the sides of the vaporizer element 42 and then output to the chemical detector device 2 via the outlet 20 where the vaporized chemical agent is analyzed and identified.

As mentioned above, the chemical detector 1 may further include the driving element 5 to drive a flow of the chemical agent aerosol into the vaporizer 40 via the inlet 10 and to further drive the vaporized chemical agent aerosol from the vaporizer 40 to the chemical detector device 2 via the outlet 20. The driving element 5 may include at least one or both of a fan 501 disposed upstream from the inlet 10 and/or a suction device 502 disposed downstream from the outlet 20. In either case, the driving element 5 may be a standalone component of the chemical detector 1 or a sub-component of the chemical agent aerosol vaporizer assembly 3.

In accordance with embodiments, the flow of the chemical agent through at least the inlet 10 and into the vaporizer 40 may be laminar so as to limit an amount of the chemical agent that is deposited on the first wall portion 31 and the central wall portion 33. The flow may be maintained in the laminar regime by cooperatively designing a flow area through the inlet 10 and into the vaporizer 40 in accordance with a design velocity of the flow.

With reference to FIGS. 2-5, the vaporizer element 42 may be provided as a finned block or structure 421, which is formed to define the fluted surface 420. The finned block 421 includes a spine portion 60 that is supportively disposed within the vaporizer 40 and a fin portion 61. The fin portion 61 includes a series of fins 610, which are disposed on and coupled to the spine portion 60 such that the fins 610 extend away from the spine portion 60 in a direction that is oppositely oriented relative to a predominant direction of the flow of the chemical agent through the inlet 10.

Figure 4:
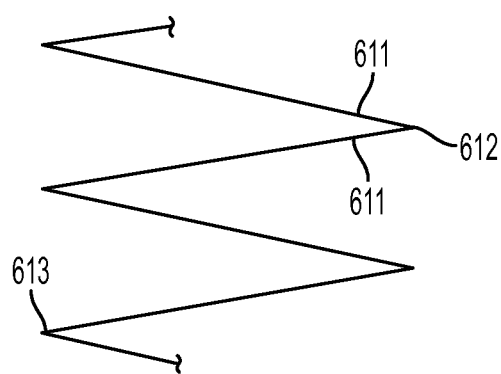
FIG. 4 is an enlarged view of a portion of the chemical agent aerosol vaporizer of FIG. 3.

As shown in FIGS. 2-4, each of the fins 610 may include surfaces 611 that are tapered toward one another with increasing distance from the spine portion 60 such that they form, for each fin 610, an elongate edge 612 running along a width-wise direction of the vaporizer element 42 and, for each pair of adjacent fins 610, an elongate trough 613 running along the width-wise direction of the vaporizer element 42. Respective angles formed by the surfaces 611 at the elongate edge 612 and at the elongate trough 613 are both acute and may be substantially similar to one another and may be substantially uniform along a height-wise direction of the vaporizer element 42.

Figure 5:
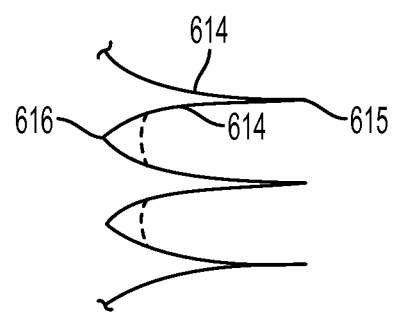
FIG. 5 is an enlarged view of a portion of a chemical agent aerosol vaporizer in accordance with alternative embodiments.

As shown in FIG. 5 and, in accordance with alternative embodiments, each of the fins 610 may include surfaces 614 that are curvilinearly tapered toward one another with increasing distance from the spine portion 60. In this case, the curvilinear surfaces 64 may form for each fin 610 a relatively sharp elongate edge 615 and, for each pair of adjacent fins 610, a sharply curved elongate trough 616 or a softly curved elongate trough (see dashed line in FIG. 5).

Figure 6:
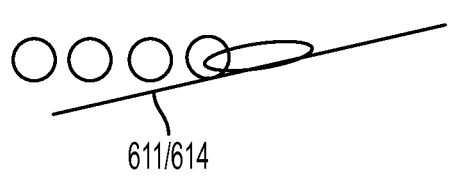
FIG. 6 is a diagrammatic illustration of a droplet of a chemical agent impacting a surface in accordance with embodiments.
Figure 7:
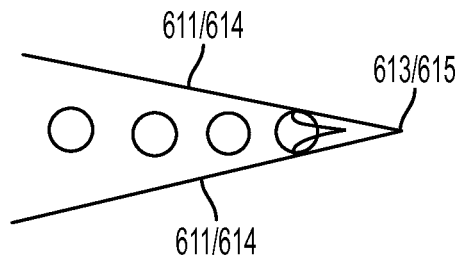
FIG. 7 is a diagrammatic illustration of a droplet of a chemical agent impacting a surface in accordance with embodiments.

With reference to FIGS. 6 and 7, for the embodiments of FIG. 2-4 or 5, a magnitude of the respective angles formed by the surfaces 611 at the elongate edge 612 and at the elongate trough 613 and by the curvilinear surfaces 614 at the sharp elongate edge 615 may be set such that the droplets of the chemical agent are encouraged to adhere to and deform along the fluted surface 420 rather than bounce off and away from the fluted surface 420. As such, the respective angles may be approximately 30 degrees or less such that the droplets impact the surfaces 611 or the curvilinear surfaces 614 with a high impact parameter or angle. In such cases, the droplets will impact, adhere to and become smeared along the fluted surface 420 at which point they can be heated and vaporized efficiently due to the high amount of droplet surface area contacting the fluted surface 420 (see FIG. 6).

For those droplets that bounce off the surfaces 611 or the curvilinear surfaces 614, their respective momentum will cause them to continue to proceed toward the elongate trough 613 or the sharply curved elongate trough 616. In such cases, the droplets will eventually impact, adhere to and become smeared along the fluted surface 420 at which point they can be heated and vaporized efficiently due to the high amount of droplet surface area contacting the fluted surface 420 (see FIG. 7).

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A chemical detector, comprising:
   a chemical detector device; and
   a chemical agent aerosol vaporizer assembly comprising
      a vaporizer fluidly interposed between an inlet and an outlet,
      the chemical agent aerosol vaporizer assembly being configured to receive via the inlet a chemical agent aerosol in the vaporizer and to direct chemical agent aerosol droplets to impact against, adhere to, and smear along a fluted surface comprising quartz or coated stainless steel that is passivated against adsorption, whereupon the aerosol is vaporized,
      the vaporized chemical agent aerosol being subsequently output to the chemical detector device via the outlet.

2. The chemical detector according to claim 1, further comprising a driving element to drive a laminar flow of the chemical agent aerosol into the vaporizer via the inlet.

3. The chemical detector according to claim 1, further comprising a heating element coupled to the fluted surface.

4. The chemical detector according to claim 1, further comprising a finned structure disposed within the vaporizer and formed to define the fluted surface.

5. The chemical detector according to claim 4, wherein the fluted surface comprises fins.

6. The chemical detector according to claim 5, wherein the fins are tapered with increasing distance from a spine portion on which the fins are disposed.

7. The chemical detector according to claim 5, wherein the fins are increasingly tapered with increasing distance from a spine portion on which the fins are disposed.

8. A chemical agent aerosol vaporizer assembly, comprising:
   an inlet;
   an outlet;
   a vaporizer fluidly interposed between the inlet and the outlet; and
   a heated, fluted surface comprising quartz or coated stainless steel disposed within the vaporizer such that chemical agent aerosol droplets received in the vaporizer via the inlet impact against, adhere to, and smear along the heated, fluted surface, which is passivated against adsorption, and vaporized,
   the vaporized chemical agent aerosol being subsequently output from the vaporizer via the outlet.

9. The chemical agent aerosol vaporizer assembly according to claim 8, further comprising a driving element to drive a laminar flow of the chemical agent aerosol into the vaporizer via the inlet.

10. The chemical agent aerosol vaporizer assembly according to claim 8, further comprising a finned block disposed within the vaporizer and formed to define the heated, fluted surface.

11. The chemical agent aerosol vaporizer assembly according to claim 10, wherein the fluted surface comprises fins.

12. The chemical agent aerosol vaporizer assembly according to claim 11, wherein the fins are one of tapered with increasing distance from a spine portion on which the fins are disposed and increasingly tapered with increasing distance from the spine portion.

13. A method of collecting a chemical agent aerosol for detection, comprising
   receiving a chemical agent aerosol via a collector inlet;
   directing droplets of the chemical agent aerosol to impact against, adhere to, and smear along a fluted surface comprising quartz or coated stainless steel that is passivated against adsorption;
   heating the fluted surface to vaporize the chemical agent aerosol on the fluted surface; and
   discharging the vaporized chemical agent aerosol via a collector outlet.

14. The method according to claim 13, further comprising driving a laminar flow of the chemical agent aerosol into the vaporizer via the inlet.

15. The method according to claim 13, wherein the fluted surface comprises fins.

16. The method according to claim 15, wherein the fins are one of tapered with increasing distance from a spine portion on which the fins are disposed and increasingly tapered with increasing distance from the spine portion.

* * * * *